United States Patent
Rowe et al.

(10) Patent No.: US 9,651,468 B2
(45) Date of Patent: May 16, 2017

(54) CLASSIFYING PARTICLE SIZE AND SHAPE DISTRIBUTION IN DRILLING FLUIDS

(71) Applicant: Halliburton Energy Services, Inc., Houston, TX (US)

(72) Inventors: Mathew Dennis Rowe, Lafayette, LA (US); Jon Troy Gosney, Bellville, TX (US); Charles Cutler Britton, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 13 days.

(21) Appl. No.: 14/890,688

(22) PCT Filed: Mar. 12, 2015

(86) PCT No.: PCT/US2015/020165
§ 371 (c)(1),
(2) Date: Nov. 12, 2015

(87) PCT Pub. No.: WO2016/133549
PCT Pub. Date: Aug. 25, 2016

(65) Prior Publication Data
US 2016/0370274 A1    Dec. 22, 2016

Related U.S. Application Data

(60) Provisional application No. 62/118,586, filed on Feb. 20, 2015.

(51) Int. Cl.
*G01N 15/02* (2006.01)
*G01V 8/02* (2006.01)
(Continued)

(52) U.S. Cl.
CPC ....... *G01N 15/0227* (2013.01); *E21B 21/065* (2013.01); *E21B 21/066* (2013.01);
(Continued)

(58) Field of Classification Search
CPC .................................................. G01N 15/0227
See application file for complete search history.

(56) References Cited

U.S. PATENT DOCUMENTS

2008/0192987 A1*  8/2008  Helgason ............... G01N 33/24
                                                    382/109
2010/0258304 A1   10/2010 Hegeman
(Continued)

FOREIGN PATENT DOCUMENTS

WO    2010116228 A2    10/2010
WO    2015002653 A1    1/2015

OTHER PUBLICATIONS

International Search Report and Written Opinion for PCT/US2015/020165 dated Oct. 16, 2015.
(Continued)

*Primary Examiner* — Tarifur Chowdhury
*Assistant Examiner* — Omar Nixon
(74) *Attorney, Agent, or Firm* — McDermott Will & Emery LLP

(57) ABSTRACT

A method includes receiving an image of drill cuttings with a data acquisition system that includes one or more processors, the drill cuttings originating from a wellbore being drilled and including a plurality of particles. The image of the drill cuttings is analyzed with the one or more processors by obtaining three two-dimensional distance measurements for each particle and obtaining four angular measurements for each particle. The one or more processors then determine at least one of a particle size distribution of the drill cuttings and a shape distribution of the drill cuttings based on the three two-dimensional distance measurements and the four angular measurements of each particle.

25 Claims, 3 Drawing Sheets

(51) Int. Cl.
*E21B 49/00* (2006.01)
*E21B 43/16* (2006.01)
*G01N 33/24* (2006.01)
*G06T 7/60* (2017.01)
*E21B 21/06* (2006.01)
*G01N 15/00* (2006.01)
*G01N 15/14* (2006.01)

(52) U.S. Cl.
CPC ............ *E21B 43/16* (2013.01); *E21B 49/005* (2013.01); *G01N 15/0205* (2013.01); *G01N 15/1475* (2013.01); *G01N 33/24* (2013.01); *G01V 8/02* (2013.01); *G06T 7/60* (2013.01); *G01N 2015/0053* (2013.01); *G01N 2015/0294* (2013.01); *G01N 2015/1497* (2013.01); *G06T 2207/30108* (2013.01)

(56) References Cited

U.S. PATENT DOCUMENTS

| | | |
|---|---|---|
| 2013/0073207 A1 | 3/2013 | Ganz |
| 2014/0009621 A1* | 1/2014 | Tucker ............... G01N 15/0227 348/159 |
| 2014/0020954 A1 | 1/2014 | Pelletier et al. |
| 2014/0046628 A1 | 2/2014 | Ligneul et al. |
| 2014/0166871 A1 | 6/2014 | Jamison et al. |
| 2014/0333754 A1* | 11/2014 | Graves ................... E21B 44/00 348/85 |
| 2015/0020588 A1* | 1/2015 | Larson .................... G01N 9/00 73/32 R |

OTHER PUBLICATIONS

Examination Report received in corresponding Netherlands Application No. NL1041678, dated Nov. 9, 2016.

* cited by examiner

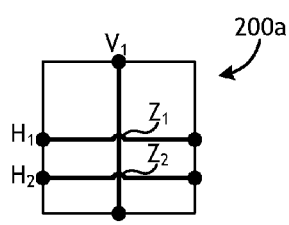
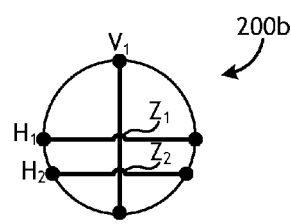
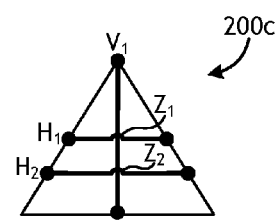
*FIG. 2A*  *FIG. 2B*  *FIG. 2C*
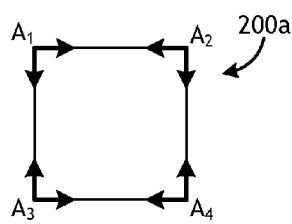
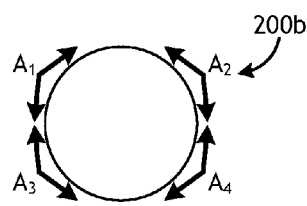
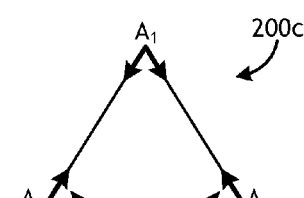
*FIG. 3A*  *FIG. 3B*  *FIG. 3C*

CLASSIFYING PARTICLE SIZE AND SHAPE DISTRIBUTION IN DRILLING FLUIDS

CROSS-REFERENCE TO RELATED APPLICATIONS

This application is a National Stage entry of and claims priority to International Application No. PCT/US2015/020165, filed on Mar. 12, 2015, which claims priority to U.S. Provisional Patent App. No. 62/118,586, filed on Feb. 20, 2015.

BACKGROUND

During the drilling of a hydrocarbon-producing well, a drilling fluid or "mud" is continuously circulated from a surface location down to the bottom of the wellbore being drilled and back to the surface again. The returning mud includes drill cuttings derived primarily from the formation being penetrated by a drill bit. In the case of multilateral wells, the drill cuttings may also include metal drill cuttings generated from milling or drilling through casing walls to form a lateral wellbore. Some downhole operations can also include borehole reaming operations, which can result in a unique type of cuttings returning to surface.

As can be appreciated, increasing the effectiveness and efficiency of drilling operations can reduce the cost of drilling wells for oil and gas exploration and subsequent production. One way of determining drilling efficiency is to observe the characteristic features of drill cuttings returning to the surface during drilling operations.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 2A-2C are three exemplary types or classes of particles that may be detected using the imaging apparatus of FIG. 1.

FIGS. 3A-3C depict the three particles of FIGS. 2A-2C and indicating exemplary angular measurements to determine angularity.

DETAILED DESCRIPTION

The present disclosure is related to wellbore drilling operations and, more particularly, to monitoring wellbore cuttings in returning drilling fluids and defining size and shape distribution of the particles present in the wellbore cuttings.

Monitoring changes in formation cutting size, size distribution, shape, and volume during active drilling operations can lead to a better understanding of the current well condition, drilling effectiveness, and hole cleaning efficiency. The connection between changes in these parameters and operational conditions may be expressed in a number of ways, including: determining the existence of over-pressured formations by detecting an increase in cutting loads and changes in the size distribution of cuttings; determining bit and drilling efficiency through analysis of cutting volume, size, and shape; determining sweep efficiency by monitoring cutting volume during a sweep operation (e.g., the volume of cuttings increases with increasing sweep efficiency, and then decreases as cuttings are moved out of the hole); and determining changes in a geological formation composition by monitoring cutting size, size distribution, and shape.

According to embodiments of the present disclosure, an imaging system may be used to monitor wellbore cuttings in returning drilling fluids and define size and shape distribution of the particles present in the wellbore cuttings in real-time or near real-time. Changes from a baseline measurement can be alarmed at an operator's console, for instance, or displayed in conjunction with the current measurements, and used to change the execution of operations (e.g., putting more or less weight on the drill bit, or changing the equivalent circulating density [ECD] of a drilling fluid, etc.). In some embodiments, an alarm may be triggered that advises the well operator that a drill bit needs be replaced.

One disclosed method includes receiving an image of drill cuttings with a data acquisition system that includes one or more processors. The data acquisition system may form part of the imaging system and the drill cuttings may originate from a wellbore being drilled and may include a plurality of particles. The image of the drill cuttings may then be analyzed with the one or more processors by obtaining three two-dimensional distance measurements for each particle and obtaining four angular measurements for each particle. The one or more processors then determine at least one of a particle size distribution of the drill cuttings and a shape distribution of the drill cuttings based on the three two-dimensional distance measurements and the four angular measurements of each particle.

Figure 1:
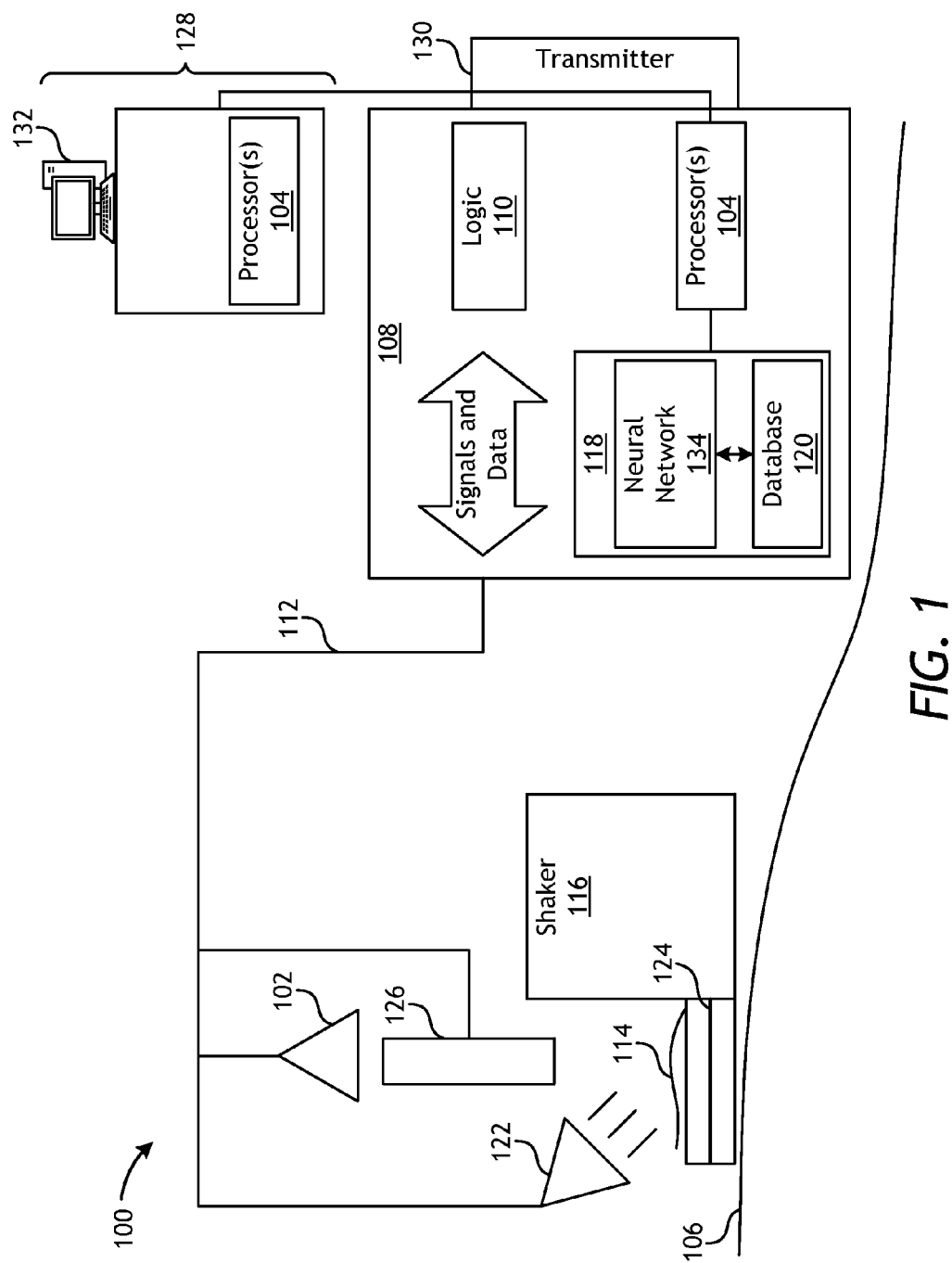
FIG. 1 is a schematic diagram of an imaging system that may be used in carrying out the principles of the present disclosure.

Referring to FIG. 1, illustrated is a schematic diagram of an imaging system 100 that may be used in carrying out the principles of the present disclosure. It should be noted, however, that the imaging system 100 is only an example of one type of imaging system, device, or apparatus that may be used in keeping with the principles of the present disclosure. Indeed, other types and configurations of imaging systems, such as flow-based imaging systems or systems that incorporate other computer design configurations, may alternatively incorporate the principles of the present disclosure, without departing from the scope of the disclosure. Accordingly, the following description of the imaging system 100 is provided for illustrative purposes only and should not be considered limiting.

As illustrated, the imaging system 100 may include one or more imaging devices 102 communicably coupled to and otherwise in communication with one or more processors 104. The imaging device 102 and/or the processors 104 may be located at a surface location 106, such as on a drill rig or at a drill site adjacent a wellbore being drilled. In some embodiments, however, any of the components in FIG. 1 may be located at a remote location, without departing from the scope of the disclosure. For instance, some of the data and processing modules may be located a remote operation center, where the data could be received and analyzed by a geologist, mud logger, or other logging professional. In addition, the remote location may comprise a mobile device, such as a tablet or handheld computer, and the data and/or resulting computational analysis may be transmitted via a data delivery system, such as Halliburton's INSITE ANYWHERE®, or via any other mobile transfer standard utilized in the industry. The imaging system 100 may also include a data acquisition system 108 that may include logic 110, perhaps comprising a programmable data acquisition subsystem. The data acquisition system 108 may be communicably coupled to the imaging device 102 via any suitable telecommunication means (e.g., wired or wireless). In operation, the imaging device 102 may provide images and/or video of drill cuttings 114 as they move across one or more shakers 116, and the logic 110 may be used to acquire image data 112 from the imaging device 102 for processing. In some embodiments, the imaging device 102 may comprise a camera that is recording data at timed intervals dependent upon the drilling operation (e.g., drilling, circulating, cleaning, etc.)

The data acquisition system 108 may further include a memory 118 communicably coupled to the processor(s) 104 and may be used to compile or store the acquired image data 112, as well as other data, perhaps in an associated database 120. The imaging device(s) 102 may comprise any type of camera capable of capturing images and/or video of the drill cuttings 114. In some embodiments, for instance, the imaging device 102 may comprise one or more CCD (charge coupled device) cameras, or one or more low light or infrared cameras. The imaging device 102 may be configured to be used in conjunction with one or more light sources 122, such as a white light source, an incandescent light source (e.g., a tungsten filament light bulb), an infrared light source, a laser, one or more light emitting diodes (LEDs), or any combination thereof.

Using a laser as the light source 122 may prove advantageous in allowing an operator to illuminate the drill cuttings 114 with a known wavelength of electromagnetic radiation. As a result, the drilling fluid and various additives suspended therein (e.g., lost circulation materials, etc.) may become relatively transparent in contrast to the adjacent drill cuttings 114 such that only the drill cuttings 114 are visible to the imaging device 102 for image capture. Alternatively, or in addition thereto, one or more energy modification devices 126, such as a polarizer, a beam splitter, and/or a filter may interpose the drill cuttings 114 and the imaging device 102 to reduce the number or breadth of wavelengths seen by the device 102. For instance, a polarizer can be used to align light energy in either the 'P' or 'S' directions (so that the processed energy is p-polarized, or s-polarized), or to generate a blend of P and S polarized energy. A beam splitter may be used to reduce the spectrum of the received energy to some selected or preferred range of wavelengths. Lastly, a filter may be used to further narrow the range to a select spectrum prior to image detection.

In some embodiments, the energy modification devices 126 may be selectively adjustable to obtain good image contrast for detection of the drill cuttings 114 within a drilling fluid solution that has a dynamic composition. The selection of materials used in the energy modification devices 126 may depend on the hazards of the environment, including the chemical solutions present. These materials may include glass, polymers, and metals, among others.

In operation, the light source 122 may be configured to illuminate the drill cuttings 114 deposited on the shaker 116, which may include one or more shaker screens 124 atop which the drill cuttings 114 traverse. The electromagnetic radiation provided by the light source 122 may intensify the images captured by the imaging device 102. The imaging device 102 may be focused on the screen 124 (or a predetermined focal plane offset from the screen 124) to capture images of the drill cuttings 114 as they move across the shaker screen 124. In other embodiments, however, the imaging device 102 may be configured to monitor the drill cuttings 114 at a point directly after the shaker 116, such as in another device (e.g., an auger discharge chute) that handles the drill cuttings 114. In yet other embodiments, the imaging device 102 may be configured to monitor a flow of the drill cuttings 114 through any conduit, piping, or interface common to the oil and gas industry.

After electromagnetic energy emitted by the drill cuttings 114 is processed by or through the energy modification devices 126 (if present), the imaging device 102 may then receive the electromagnetic energy and transmit image data 112 of the drill cuttings 114 to the data acquisition system 108 for processing. In some embodiments, the data acquisition system 108 may comprise and otherwise form part of a remote workstation 128. In other embodiments, the data acquisition system 108 may be configured to communicate with the remote workstation 128 via a transmitter 130, which may include any form of wired or wireless telecommunication such as, but not limited to, wires, fiber optics, wireless means (e.g., radio frequency, etc.). In such embodiments, the image data 112 of the drill cuttings 114 may be transmitted to the remote workstation 128 to be processed with associated processors 104.

Processing the image data 112 of the drill cuttings 114 may result in the determination of various characteristics of the drill cuttings 114, such as particle size and shape distribution of the particulate matter suspended within the drill cuttings 114. As described in greater detail below, the processors 104 may be programmed to define the angularity of the particles detected in the drill cuttings 114 and thereby classify the particles into shape classes. The data acquisition system 108 and/or the remote workstation 128 may include one or more peripheral devices 132, such as a computer screen, a graphical user interface, a hand-held device, a printer, or any combination thereof. The peripheral devices 132 may provide an operator with a graphical display of the results of processing the image data 112 of the drill cuttings 114.

The data acquisition system 108 may be generally characterized as a computer or computer system and the computer hardware associated with the data acquisition system 108, such as the processor(s) 104, may be used to implement the various methods and algorithms described herein. More particularly, the processor(s) 104 may be configured to execute one or more sequences of instructions, programming stances, or code stored on a non-transitory, computer-readable medium, such as the memory 118. The processor 104 can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. The memory 118 may comprise at least one of include random access memory (RAM), flash memory, read only memory (ROM), programmable read only memory (PROM), and electrically erasable programmable read only memory (EEPROM). The memory 118 may further include one or more of registers, hard disks, removable disks, CD-ROMS, DVDs, or any other like suitable storage device or medium.

Executable sequences described herein can be implemented with one or more sequences of code contained in the memory 118. In some embodiments, such code can be read into the memory 118 from another machine-readable medium. Execution of the sequences of instructions contained in the memory can cause the processor 104 to perform the process steps described herein. As will be appreciated, one or more processors 104 in a multi-processing arrangement can also be employed to execute instruction sequences in the memory 118. In addition, hard-wired circuitry can be used in place of or in combination with software instructions to implement various embodiments described herein. Thus, the present embodiments are not limited to any specific combination of hardware and/or software.

Upon receiving the images derived from the imaging device 102, the data acquisition system 108 may make or undertake a variety of measurements on the plurality of particles suspended within the drill cuttings 114. More particularly, a software program stored in the memory 118 (e.g., the database 120) may be programmed with instructions that, when executed by the processor(s) 104, perform the desired measurements on the plurality of particles. The software may be programmed to recognize boundaries or edges of the particles by detecting contrast between a given particle and its surroundings.

Referring to FIGS. 2A, 2B, and 2C, with continued reference to FIG. 1, illustrated are three exemplary types or classes of particles 200a, 200b, and 200c that may be detected or otherwise monitored using the imaging system 100 of FIG. 1, according to one or more embodiments. The particles 200a-c may be entrained in the drill cuttings 114 and one or more images of the particles 200a-c may be captured with the imaging device 102 and transmitted to the data acquisition system 108 in the form of image data 112 for processing. As illustrated, the first particle 200a is generally square, the second particle 200b is generally circular, and the third particle 200c is generally triangular.

Those skilled in the art will readily recognize that cubic, rounded, and pyramidal shapes comprise the three basic shapes for particles that may be entrained in drill cuttings 114. The first particle 200a may be indicative of a generally cubic-shaped particle entrained in the drill cuttings 114. Cubic particles may indicate the presence of "pop-offs," which comprise a cube of material that has dislodged or "popped-off" the wall of the wellbore during drilling operations. Pop-offs may result from underbalanced pressures within the wellbore and the density of pop-off particles may be a good indicator of healthy or unhealthy pore pressures. Identifying cubic particles may prove especially advantageous in managed pressure drilling applications, where an operator may decide to apply more backpressure at the surface pumps or by manipulating surface chokes, or alter the weight of the drilling fluid with additives upon affirmatively identifying cubic particles.

The second particle 200b may be indicative of spherical or rounded particles entrained in the drill cuttings 114. Spherical particles may indicate the presence of well-worn sand downhole or that tumbling is occurring within the wellbore. The third particle 200c may be indicative of generally pyramidal cuttings, which are typically derived from rock formations penetrated by certain types of drill bits and mills. For instance, drill bits and mills that use polycrystalline diamond compact cutters can also discharge generally pyramidal-shaped or truncated pyramidal-shaped particles while penetrating rock formations during drilling operations. While the most common type of particle resulting from reaming operations to enlarge a borehole diameter is a cubic or block-type particle (i.e., the first particle 200a of FIG. 2A), pyramidal-shaped or truncated pyramidal-shaped particles can also result from reaming operations.

Upon receiving the images of the particles 200a-c in the data acquisition system 108, the processor 104 may be configured to obtain three two-dimensional distance measurements for each particle 200a-c. To accomplish this, the processor 104 may first determine and otherwise superimpose orthogonal X and Y axes on the particles 200a-c. The longer of the X and Y axes may be characterized as the X-axis and labeled as a first measurement or length $V_1$, and the shorter of the X and Y axes may be characterized as the Y-axis and labeled as a second measurement or width $H_1$. The width $H_1$ may bisect $V_1$ and otherwise be measured at the mid-way point between the ends of the length $V_1$. A third measurement or intermediate width $H_2$ may be measured at the mid-way point between $H_1$ and either end of $V_1$. As illustrated, the intermediate width $H_2$ may be measured orthogonal to $V_1$ such that the width $H_1$ and intermediate width $H_2$ extend parallel to one another. As will be appreciated, by obtaining the third measurement for the intermediate width $H_2$, the degrees of freedom in determining particle shape and size may be greatly reduced.

By comparing the size of each measurement $V_1$, $H_1$, $H_2$, it may be determined whether the particle under inspection is generally square, generally circular, or generally triangular. More particularly, if $V_1 \approx H_1 \approx H_2$ for a given particle, then the given particle is likely square shaped, such as the first particle 200a. If, however, $V_1 \approx H_1 > H_2$ for a given particle, then the given particle is likely circle shaped, such as the second particle 200b. Moreover, if $V_1 > H_1 < H_2$ for a given particle, then the given particle is likely triangular shaped, such as the third particle 200c. Accordingly, the three distance measurements $V_1$, $H_1$, $H_2$ may provide a base category of shape for each particle 200a-c: square, circular, and triangular. In cases where the aspect ratio between $V_1$ and $H_1$ is about 1/1000 for a given particle, the given particle may be characterized and otherwise defined as a long and slender rod.

In some embodiments, the shape of the drill cuttings 114 may be monitored to determine a size distribution that exists in three-dimensional space. As a basic example, the size distribution of the particles 200a-c within the drill cuttings 114 may be determined by averaging the three measurements $V_1$, $H_1$, $H_2$ together for each detected particle 200a-c and then dividing by three. More particularly, the average particle size for a selection of particles, at least two, will be divided into bins based on a size range. The divisions will include at least two bins, but could include a hundred or more bins based on the variability of size of the particles. Each bin could account for particle change in size on the order of microns, for example, but could alternatively be on the order of any measurement division. Additionally, a three-dimensional size distribution could be determined. The length $V_1$ can be handled on a separate axis than the arithmetic mean of $H_1$ and $H_2$ against an axis with bins as previously stated to produce a plane with size distributions.

Another method to determine size distribution may include determining a statistical size distribution using at least a t, z, or chi distribution of the particles based on the average of the three measurements of a minimum of three particles, the length $V_1$ of a minimum of three particles, or any other measurement made. As will be appreciated, the t, z or chi distributions may provide the range of particles seen based on the average and variance in size of the particles. Accordingly, when the imaging system 100 identifies the basic shape of the particles 200a-c being monitored, a distribution of the various sizes may be calculated. This may prove advantageous in helping to determine downhole conditions.

As will be appreciated, obtaining the three distance measurements $V_1$, $H_1$, $H_2$ may result in defining the relationship for many particle shapes, but it may not be evident whether a given particle exhibits a curved shape, as in terms of a circle, or has hard angles, like a square, a triangle, or other type of polygon. Accordingly, embodiments of the present disclosure further include defining the angularity of the particles $200a$-$c$ within the drill cuttings 114 using four angular measurements, and thereby helping to further discriminate between the three basic measurement classes: square, circular, and triangular.

Referring to FIGS. 3A, 3B, and 3C, illustrated are the three particles $200a$-$c$ of FIGS. 2A-2C indicating exemplary angular measurements to determine angularity, according to one or more embodiments. As illustrated, angularity of the particles $200a$-$c$ may be determined by measuring at least four angles on each particle $200a$-$c$, shown as a first angle $A_1$, a second angle $A_2$, a third angle $A_3$, and a fourth angle $A_4$. Upon receiving the images of the particles $200a$-$c$ in the data acquisition system 108, the processor 104 may be configured to obtain measurements for the four angles $A_1$-$A_4$. In some embodiments, the processor 104 may be configured to determine where to locate the angles based on the contrast between the given particle and the background surrounding the particle. In some embodiments, the location of each angle measurement may be equidistantly spaced from each other about the border of the given particle, unless the particle is pyramidal. If the particle is pyramidal in shape, three angles will be measured at the three apexes of the triangular shape. In other embodiments, however, the location of the angles may be determined as dictated by the particular software being implemented in the imaging system 100.

The four angles $A_1$-$A_4$ may be measured to determine how square, rounded, or triangular a given particle $200a$-$c$ is. The angularity of the given particle $200a$-$c$ may be calculated as the sum of the four angles $A_1$-$A_4$ and will be between 180° and 720°. Sums that are closer to 180° will be considered highly angular and likely correspond to a triangular structure, and sums that are closer to 720° will be considered substantially non-angular and likely correspond to a circular structure. By comparing measurements for the four angles $A_1$-$A_4$ of a given particle $200a$-$c$ it can be determined whether the given particle $200a$-$c$ is more square, round, or triangular. For instance, if $A_1 \approx A_2 \approx A_3 \approx A_4$ for a given particle, and the four angles $A_1$-$A_4$ range between about 70° and about 110°, then the given particle is likely square shaped, such as the first particle $200a$. If however, $A_1 \approx A_2 \approx A_3 \approx A_4$ for a given particle, and the four angles $A_1$-$A_4$ are all greater than 90°, then the given particle is likely circle shaped, such as the second particle $200b$. Moreover, if $A_1 \approx A_2 \approx A_3$ and $A_4 = 0$ for a given particle, and the sum of the measured three angles $A_1$-$A_3$ is approximately 180°, then the given particle is likely triangle shaped, such as the third particle $200c$.

With three measured distances $V_1$, $H_1$, $H_2$ and four measured angles $A_1$-$A_4$, most shapes of the particles $200a$-$c$ can be distinguished and classified with the data acquisition system 108 as either square, circular, or triangular. To convert these measurements into three-dimensional space, however, and thereby classify the particles $200a$-$c$ as generally cubic, spherical or pyramidal, an additional two distance measurements and an additional two angular measurements may be obtained. In such embodiments, at least two imaging devices 102 may be employed to determine the relative depth of each particle $200a$-$c$. More particularly, and with reference again to FIGS. 2A-2C, a first imaging device 102 may be configured to obtain a fourth distance measurement $Z_1$ in the Z-direction (i.e., out of the page in FIGS. 2A-2C) at the intersection of $H_1/V_1$, and a second imaging device 102 may be configured to obtain a fifth distance measurement $Z_2$ in the Z-direction at the intersection of $H_2/V_1$. The Z-direction is further defined as 90° from $H_1$ or $H_2$ (depending on which measurement is being taken) and perpendicular to $V_1$.

The fourth measurement $Z_1$ may correspond to the focal plane associated with of the first imaging device 102, and the fifth measurement $Z_2$ may correspond to the focal plane of the second imaging device 102. The focal plane of each imaging device 102 may lie where captured images for the imaging device 102 are clear or in focus (i.e., little or no distortion of objects at the focal plane). By adjusting focusing elements and lenses of the imaging devices 102, the focal plane for the imaging devices 102 may be selected to lie at a known depth (or distance) along the Z-axis, such that the difference between the focal planes of each imaging device 102 may be known. By measuring the "clarity" or the distortion (i.e., lack of definition) of the retrieved images of the particles $200a$-$c$ in each focal plane at the intersections $H_1/V_1$ and $H_2/V_1$, the data acquisition system 108 may be able to ascertain depth measurements for $Z_1$ and $Z_2$. More particularly, the distortion of the images may be compared against a known reference point, which may be any permanent fixture from which the data acquisition system 108 may discern the magnitude (e.g., percentage) of distortion of the image at the intersections $H_1/V_1$ and $H_2/V_1$. In some embodiments, for instance, the reference point may be the upper surface of the shaker screen 124, but a virtual reference point may alternatively be programmed into the data acquisition system 108, without departing from the scope of the disclosure.

In operation, the processor 104 may be configured to calculate the amount of distortion of the particle $200a$-$c$ at each focal plane at the intersections $H_1/V_1$ and $H_2/V_1$ as a function of depth. By referencing the reference point, a model stored in the database 120 may be applied and reference the reference point in generating or otherwise providing a percentage of distortion. The model can be a distortion model that provides known percentages of clarity or distortion that may be compared against to determine the depth of the fourth and fifth measurements $Z_1$ and $Z_2$ at the intersections $H_1/V_1$ and $H_2/V_1$, respectively. Since the difference between the focal planes or detection depths of each imaging device 102 is known, a comparison of the fourth and fifth measurements $Z_1$ and $Z_2$ at the intersections $H_1/V_1$ and $H_2/V_1$ may result in a difference in depth, which may provide an indication of three-dimensional contours for the particles $200a$-$c$.

In addition, besides determining and measuring the four angles $A_1$-$A_4$, as discussed above, the processor 104 may be configured to ascertain and measure two additional angular measurements to help map a given particle $200a$-$c$ in three-dimensional space. For particles that are generally square or circular, such as the first and second particles $200a,b$, respectively, the additional angular measurements may be obtained in a plane that is perpendicular to the plane intersecting the four angles $A_1$-$A_4$. For particles that are generally triangular, such as the third particle $200c$, the additional angular measurements may be obtained in a plane that is perpendicular to the base of the triangular particle $200c$.

The two additional angular measurements may be determined based on the focal planes of the imaging devices 102 and the detected loss of clarity at the boundaries of the particles $200a$-$c$ based on contrast. With multiple imaging devices 102 configured at different focal planes, the change in clarity as a function of depth can be determined. A simple linear line, or other mathematical function to produce a line, can be fitted to the rate in change of clarity. When the rate in change of clarity changes, a second line can be fitted. The two lines can be assumed to be in a single plane and an angle can be determined between the two fitted lines.

Referring again to FIG. 1, the data acquisition system 108 may further include a neural network 134 that may be programmed into the memory 118. The neural network 134 may be used to help the processor 104 recognize the distances $V_1$, $H_1$, $H_2$, $Z_1$, $Z_2$ and the angles $A_1$-$A_4$ in determining shape, size, and volume of the particles 200a-c. More particularly, the neural network 134 may be trained prior to deployment using one or more kits or collections of physical objects of a known shape, size, and volume. Such physical objects may be provided from a variety of sources to provide a set of training data for the neural network 134. In some embodiments, for instance, the physical objects may comprise ordinary physical objects, such as ball bearings, cubes, pyramids, etc., or any three dimensional objects of a known or determinable shape, size, and volume.

In other embodiments, the physical objects used in training the neural network 134 may comprise drill cuttings derived from the current well being drilled. Resultant drill cuttings from the current well, for example, may be sampled, cleaned, and analyzed using an offline analysis system that assists in calibrating the data acquisition system 108. Known image data may then be uploaded back into the software for training the neural network. In yet other embodiments, the physical objects used in training the neural network 134 may comprise drill cuttings derived from an adjacent well (e.g., an offset well, a side-track well, a bypass well, etc.) since the geology of adjacent wells should be substantially similar (assuming use of the same type and size of drill bits in obtaining the drill cuttings). In such cases, samples of the drill cuttings obtained from the adjacent well may be cleaned, weighed, and scanned to determine the shape, size, and volume of the particles entrained therein. The drill cuttings may then be run through the imaging system 100 to correlate the now-known characteristics of the particles (i.e., shape, size, and volume) to the measurements obtained by the imaging system 100. The resulting data may be stored in the database 120 for future reference by the neural network 134 when subsequently monitoring the drill cuttings 114 in real-time.

When multiple wells are drilled in the same field and/or on the same drill rig, the database 120 may be populated with training data sets corresponding to known characteristics of sample drill cuttings derived from each well. Various drilling parameters may also be stored in the database 120 and associated with each training data set. For instance, drilling parameters such as the configuration of the bottom-hole assembly used, the drilling fluid type, the weight-on-bit, and the true vertical depth may be stored in the database 120 for each training data set. In real time, the neural network 134 may query the database 120 when monitoring drill cuttings 114 derived from a well under similar drilling parameters as compared to the stored training data sets. As will be appreciated, this may prove advantageous in monitoring new wells where the database 120 may be used to match similar bottom-hole assemblies, drilling fluid types, weight-on-bit, and true vertical depth, and thereby provide an initial training set without having prior data from the actual well being drilled.

In some embodiments, the imaging system 100 may further be configured to monitor and otherwise detect the presence of metal shavings or cuttings in the drill cuttings 114. Metal cuttings may be differentiated and otherwise distinguishable from the particles 200a-c in the drill cuttings 114 due to the high ratio of $V_1$ to $H_1$. For instance, metal cuttings can exhibit a $V_1/H_1$ ratio greater than 1,000. Metal cuttings may result from a variety of sources. In some cases, for instance, metal cuttings may be generated while milling or otherwise drilling through the casing wall or a pre-milled window to create a casing exit for a multilateral well. The density of the metal cuttings as detected by the imaging device 100 may inform an operator as to when the mill has fully penetrated the casing wall, and thereby indicate that the casing exit is complete. For instance, the cuttings from a milling operation typically comprise long metal shavings, akin to cuttings often seen in a machine shop. If long shavings are not present during milling, and instead fine shavings are present, then this may be an indication that no progress is being made and surface actions may be required (i.e., increasing the weight on the mill, determining and/or adjusting the torque on the mill, pulling the mill out of the hole, replacing the mill, etc.). Accordingly, the metal cuttings may be monitored to ensure proper hole cleaning and to determine if the mill used to cut through wall of the casing is functioning efficiently.

In other cases, however, metal cuttings may be an indication that the casing that lines the wellbore is being inadvertently nicked or cut into while running a mill or drill bit downhole. Based on the known flow rate of the drilling fluid circulating through the wellbore, an operator may be able to determine the approximate location in the wellbore where the metal cuttings originated. In such cases, an inspection tool (i.e., a bond logging tool) may be conveyed into the wellbore to inspect the area where the metal cuttings originated and ascertain whether repairs to the casing are needed.

In some embodiments, the data acquisition system 108 may further be configured to determine the mass of the drill cuttings 114 (FIG. 1). This may be accomplished by ascertaining the volume rate of the drill cuttings 114 being detected and a density of the drill cuttings 114. The volume rate of the drill cuttings 114 may be determined through the use of flow meters or other known flow-measurement devices. In some cases, the density of the drill cuttings 114 may be determined by obtaining density information from measurement-while-drilling (MWD) or logging-while-drilling (LWD) tools used in a drilling operation. In such cases, MWD or LWD density sensors, such neutron density sensors that determine bulk density of formation cuttings, may analyze the formation being penetrated and transmit bulk formation density data to the data acquisition system 108 for processing. In other cases, however, the density of the drill cuttings 114 may be determined by extracting a sample of the drill cuttings 114 and determining its mass by weighing the sample and thereby determining the volume. The measured volume rate of the drill cuttings 114 may then be multiplied by the measured density, which will result in the mass rate of the drill cuttings 114.

The processed information generated by the data acquisition system 108 (e.g., cutting shape, size, volume, etc.) may then be provided to a well operator via the one or more peripheral devices 132 to show real-time or near real-time changes to the drill cuttings 114 that occur during drilling operations. As will be appreciated, determining the changes in the particle size and distribution of the drill cuttings 114 may prove advantageous in ascertaining the operational conditions that are likely to be associated with those types of changes and the probable conditions. These conditions may then be used to implement intelligent control of the drilling operation, such as adjusting the weight-on-bit, adjusting the equivalent circulating density of the drilling fluid, adding additives to the drilling fluid, or halting drilling operations altogether.

Still referring to FIG. 1, according to further embodiments of the present disclosure, the accuracy of the imaging system 100 may be evaluated and otherwise ascertained to demonstrate to a well operator that the imaging system 100, or any other imaging or scanning apparatus used to determine the shape, volume, and size distribution of the drill cuttings 114, is operating as designed. More particularly, a verification system or program may be employed in concert with the neural network 134. In some embodiments, the verification system may comprise, at least in part, a software program stored in the memory 118 of the data acquisition system 108 and programmed with instructions that, when executed by the processor(s) 104, perform desired measurement verification steps. In other embodiments, the verification program may comprise any other system that may be programmed to verify at least two different types of measured characteristics of the drill cuttings 114: volume and particle size distribution. Each type of measurement verification is discussed below.

For volume measurement verification, a first kit of physical objects of a known volume may be provided to the verification system (e.g., the data acquisition system 108). The first kit may comprise a variety of three-dimensional objects having dimensions that are within the scanning range of the imaging system 100. For instance, these objects can include purchased items of a known volume, such as objects that have been manufactured to a high-accuracy known volume, or objects for which their volume can be readily calculated, such as ball bearings, cubes, pyramids, etc. In other cases, these objects may exhibit a known volume as previously measured or determined by means such as displacement or other higher accuracy scanning means (e.g., a coordinate measuring machine). In operation, these physical objects may be measured or scanned by the imaging system 100 to determine if the measured volume of the objects is close to the known volume of the objects and, therefore, whether the imaging system 100 is operating within a predetermined accuracy threshold. In some embodiments, a total weight of the first kit of physical objects may be used to verify that all the objects for the first kit are present.

In volume measurement verification, the imaging system 100 may employ two imaging devices 102, each with corresponding focal planes, as described above, and may be configured to determine the depth of the physical objects based on the detected or measured distortion (i.e., lack of definition) of the captured images. As discussed above, the measured distortion, which can be in the form of a percentage, can be associated with the volume of the physical objects being measured. Accordingly, objects of a known volume and size are monitored by the imaging system 100 and the resulting measurements are compared against the known parameters and measurements of the objects to determine if the imaging system 100 is operating properly or within the accuracy threshold. If the imaging system 100 falls outside of the accuracy threshold, the imaging system 100 may then be recalibrated, if desired, which may include re-training the neural network 134 with new training data sets, as discussed above.

For size distribution verification, a second kit of physical objects may be provided to the verification system (e.g., the data acquisition system 108). In some embodiments, the first and second kits of physical objects may be the same. In other embodiments, however, the first and second kits of physical objects may be distinct. The objects in the second kit may again be commercially available objects of a known size distribution and aspect ratio or specially manufactured items with a known range of size distribution and aspect ratios. In some cases, the objects of the second kit may be of the same geometry but of different sizes, or may alternatively be of different geometries and different sizes. As will be appreciated, the sizes of the objects used will be generally within the particle size specification of the imaging system 100.

The differently-sized objects of the second kit may be mixed in a known ratio (i.e., size distribution) and run through the imaging system 100 for detection. The known ratio may then be compared to the measured and calculated size distribution as provided by the imaging system 100 to determine if the imaging system 100 is reading within the specified tolerance and otherwise within the predetermined accuracy threshold of the imaging system 100. As with the first kit of physical objects, a total weight of the second kit may be used to verify that all the objects for the third kit are present.

In some embodiments, any of the objects in the first and/or second kits of physical objects may further vary in reflectance and surface smoothness. As a result, such objects may be used to test if these parameters also affect the scanning results of the imaging system 100. This may prove advantageous in training the imaging system 100 to differentiate between metallic, crystalline, and matted objects, each of which may affect the contrast ratio of the particles 200a-c based on how the light (i.e., from the light source 122) impinges upon the outer surfaces of the particles 200a-c. The neural network 134 may be trained to accept the most effective contrast ratio based on what type of particle 200a-c is being detected. In some cases, the neural network 134 may be trained to utilize the best light source 122 to improve the contrast ratio. In such cases, various light sources 122 may be switched on/off to improve the contrast ratio based on the particle and background lighting conditions.

Accordingly, the verification system may be configured to use physical objects of a known size and geometry to test the specified limits of the imaging system 100. This type of system may be used for verifying the determination of volume and size distribution of the well cuttings 114. The presently described verification system uses a known input and compares that to the measured and calculated results of the imaging system 100 and thereby provides a direct means of demonstrating whether the imaging system 100 is operating as desired.

Figure 4:
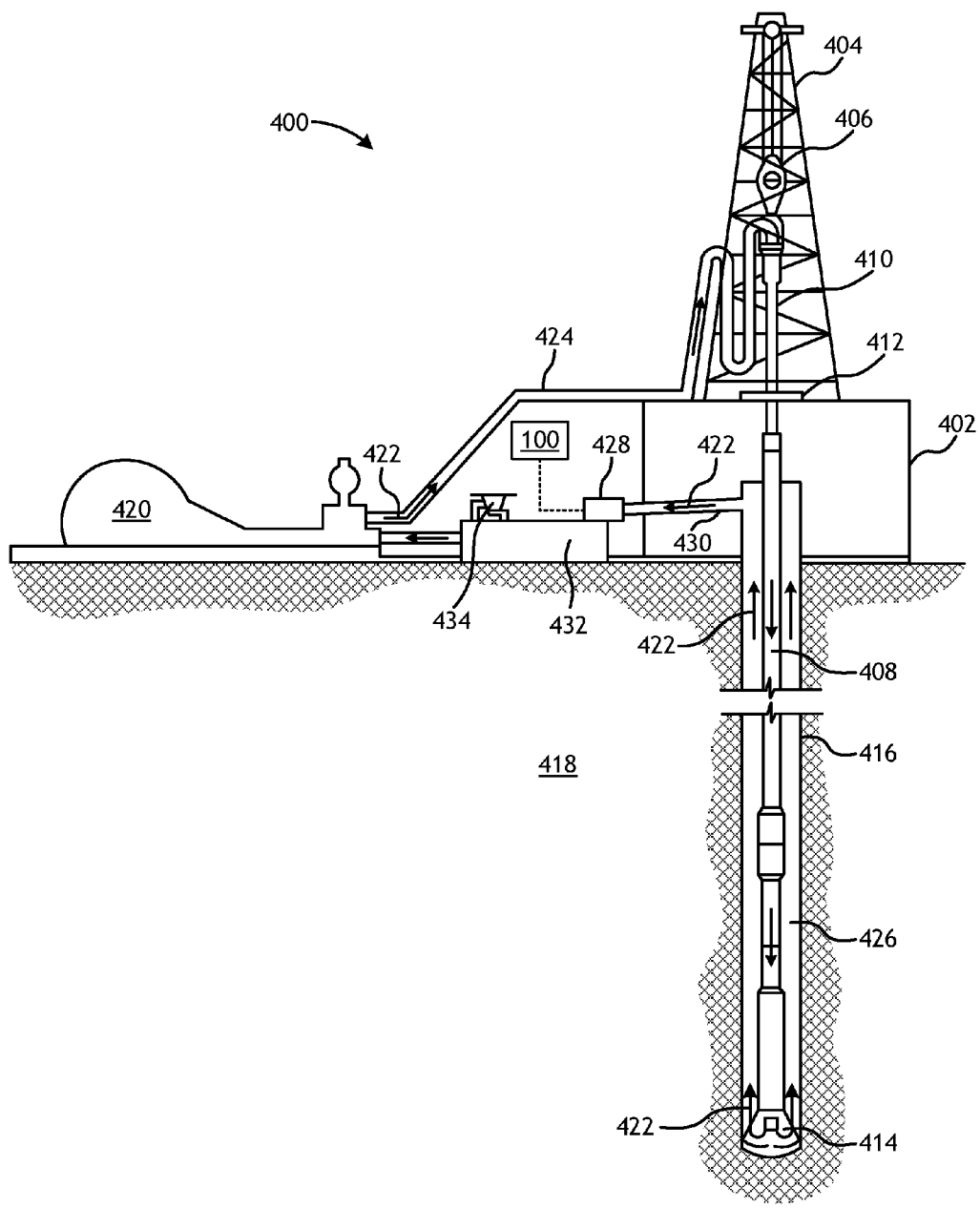
FIG. 4 is a schematic diagram of an exemplary drilling system that may include the imaging system of FIG. 1.

Referring now to FIG. 4, illustrated is an exemplary drilling system 400 that may include the imaging system 100, according to one or more embodiments of the present disclosure. It should be noted that while FIG. 1 generally depicts a land-based drilling assembly, those skilled in the art will readily recognize that the principles described herein are equally applicable to subsea drilling operations that employ floating or sea-based platforms and rigs, without departing from the scope of the disclosure. As illustrated, the drilling system 400 may include a drilling platform 402 that supports a derrick 404 having a traveling block 406 for raising and lowering a drill string 408. The drill string 408 may include, but is not limited to, drill pipe and coiled tubing, as generally known to those skilled in the art. A kelly 410 supports the drill string 408 as it is lowered through a rotary table 412. A drill bit 414 is attached to the distal end of the drill string 408 and is driven either by a downhole motor and/or via rotation of the drill string 408 from the well surface. As the bit 414 rotates, it creates a borehole 416 that penetrates various subterranean formations 418.

A pump 420 (e.g., a mud pump) circulates drilling fluid 422 through a feed pipe 424 and to the kelly 410, which conveys the drilling fluid 422 downhole through the interior of the drill string 408 and through one or more orifices in the drill bit 414. The drilling fluid 422 is then circulated back to the surface via an annulus 426 defined between the drill string 408 and the walls of the borehole 416. At the surface, the recirculated or spent drilling fluid 422 exits the annulus 426 and may be conveyed to one or more fluid processing unit(s) 428 via an interconnecting flow line 430. After passing through the fluid processing unit(s) 428, a "cleaned" drilling fluid 422 is deposited into a nearby retention pit 432 (i.e., a mud pit). One or more chemicals, fluids, or additives may be added to the drilling fluid 422 via a mixing hopper 434 communicably coupled to or otherwise in fluid communication with the retention pit 432.

The fluid processing unit(s) 428 may include and otherwise be the same as the shaker(s) 116 of FIG. 1. As illustrated, the imaging system 100 may be communicably coupled to and otherwise incorporate the fluid processing unit(s) 428 where, as described above, the imaging device 102 (FIG. 1) may capture images of the drill cuttings 114 (FIG. 1) returning in the drilling fluid 422 and transmit the image data 112 (FIG. 1) to the data acquisition system 108 (FIG. 1) for processing.

As used herein, a machine-readable medium will refer to any medium that directly or indirectly provides instructions to the processor(s) 104 for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A method that includes receiving an image of drill cuttings with a data acquisition system that includes one or more processors, the drill cuttings originating from a wellbore being drilled and including a plurality of particles, analyzing the image of the drill cuttings with the one or more processors by obtaining three two-dimensional distance measurements for each particle and obtaining four angular measurements for each particle, and determining with the one or more processors at least one of a particle size distribution of the drill cuttings and a shape distribution of the drill cuttings based on the three two-dimensional distance measurements and the four angular measurements of each particle.

B. A non-transitory, computer-readable medium programmed with computer executable instructions that, when executed by a processor of a computer unit, perform the method of receiving an image of drill cuttings with a data acquisition system that includes one or more processors, the drill cuttings originating from a wellbore being drilled and including a plurality of particles suspended, analyzing the image of the drill cuttings with the one or more processors by obtaining three two-dimensional distance measurements for each particle and obtaining four angular measurements for each particle, and determining with the one or more processors at least one of a particle size distribution of the drill cuttings and a shape distribution of the drill cuttings based on the three two-dimensional distance measurements and the four angular measurements of each particle.

Each of embodiments A and B may have one or more of the following additional elements in any combination: Element 1: wherein receiving the image of the drill cuttings with the data acquisition system is preceded by conveying the drill cuttings across a shaker screen of a shaker, capturing images of the drill cuttings at or after the shaker screen with one or more imaging devices and thereby generating image data, and transmitting the image data to the data acquisition system. Element 2: further comprising illuminating the drill cuttings at or after the shaker screen with a light source that emits a known wavelength of electromagnetic radiation, wherein the light source is selected from the group consisting of a white light source, an incandescent light source, an infrared light source, a laser, one or more light emitting diodes, and any combination thereof. Element 3: wherein the light source includes a plurality of light sources, the method further comprising switching between the plurality of light sources and thereby improving a contrast ratio for at least some of the plurality of particles. Element 4: wherein obtaining the three two-dimensional distance measurements for each particle comprises identifying and measuring a length for each particle, identifying and measuring a width for each particle, wherein the measurement for the width bisects the length and is orthogonal thereto, and identifying and measuring an intermediate width for each particle, wherein the measurement for the intermediate width is obtained at a mid-way point between an intersection between the length and the width and is orthogonal to the length. Element 5: further comprising comparing measurements for the length, the width, and the intermediate width for a given particle to determine whether the given particle is square, circular, or triangular. Element 6: further comprising averaging measurements for the length, the width, and the intermediate width for each particle to determine a statistical size distribution of the plurality of particles within the drill cuttings. Element 7: wherein a given particle of the plurality of particles is identified as a square-shaped particle when the four angular measurements each range between about 70° and about 110°. Element 8: wherein a given particle of the plurality of particles is identified as a circular-shaped particle when the four angular measurements are each greater than 90°. Element 9: wherein the four angular measurements comprise a first angle, a second angle, a third angle, and a fourth angle, and wherein a given particle of the plurality of particles is identified as a triangle-shaped particle when the fourth angle is zero and a sum of the first, second, and third angles is about 180°. Element 10: further comprising classifying each particle with the one or more processors as one of square, circular, and triangular as based on the three two-dimensional distance measurements and the four angular measurements. Element 11: further comprising capturing images of each particle with at least a first imaging device and a second imaging device, wherein the first imaging device captures images at a first focal plane and the second imaging device captures images at a second focal plane that is different from the first focal plane; analyzing the images of each particle from the first and second imaging devices with the one or more processors and obtaining a first depth measurement associated with the first imaging device and a second depth measurement associated with the second imaging device for each particle; and determining with the one or more processors a three-dimensional shape of each particle based on the three two-dimensional distance measurements, the four angular measurements, and the first and second depth measurements, wherein the three-dimensional shape is selected from the group consisting of a cube, a sphere, and a pyramid. Element 12: wherein the data acquisition system further comprises a neural network that includes training data sets based on one or more collections of physical objects of a known shape, size, and volume, and wherein determining with the one or more processors at least one of the particle size distribution and the shape distribution of the drill cuttings further comprises training the neural network with the one or more collections of physical objects to generate the training data sets, and querying the neural network with the one or more processors to correlate the known shape, size, and volume of the training data sets to the measurements obtained by the one or more processors. Element 13: further comprising determining a volume rate of the drill cuttings, determining a density of the drill cuttings, and multiplying the volume rate of the drill cuttings with the density of the drill cuttings and thereby obtaining a mass rate of the drill cuttings. Element 14: further comprising displaying the at least one of the particle size distribution of the drill cuttings and the shape distribution of the drill cuttings on one or more peripheral devices communicably coupled to the data acquisition system. Element 15: wherein the data acquisition system forms part of an imaging system that includes one or more imaging devices that obtain the image of drill cuttings, the method further comprising sampling a kit of physical objects of a known volume with the one or more imaging devices and thereby obtaining measured volumes with the data acquisition system, sampling a kit of physical objects of a known size distribution with the one or more imaging devices and thereby obtaining a measured size distribution with the data acquisition system, and determining if the imaging system operates within a predetermined accuracy threshold by comparing at least one of the measured volumes against the known volume and the measured size distribution against the known size distribution. Element 16: further comprising re-calibrating the imaging system when it is determined that the imaging system is operating without the predetermined accuracy threshold.

Element 17: wherein obtaining the three two-dimensional distance measurements for each particle comprises identifying and measuring a length for each particle, identifying and measuring a width for each particle, wherein the measurement for the width bisects the length and is orthogonal thereto, and identifying and measuring an intermediate width for each particle, wherein the measurement for the intermediate width is obtained at a mid-way point between an intersection between the length and the width and is orthogonal to the length. Element 18: further comprising comparing measurements for the length, the width, and the intermediate width for a given particle to determine whether the given particle is square, circular, or triangular. Element 19: further comprising averaging measurements for the length, the width, and the intermediate width for each particle to determine a statistical size distribution of the plurality of particles within the drill cuttings. Element 20: further comprising classifying each particle with the one or more processors as one of square, circular, and triangular as based on the three two-dimensional distance measurements and the four angular measurements. Element 21: further comprising capturing images of each particle with at least a first imaging device and a second imaging device, wherein the first imaging device captures images at a first focal plane and the second imaging device captures images at a second focal plane that is different from the first focal plane, analyzing the images of each particle from the first and second imaging devices with the one or more processors and obtaining a first depth measurement associated with the first imaging device and a second depth measurement associated with the second imaging device for each particle, and determining with the one or more processors a three-dimensional shape of each particle based on the three two-dimensional distance measurements, the four angular measurements, and the first and second depth measurements, wherein the three-dimensional shape is selected from the group consisting of a cube, a sphere, and a pyramid. Element 22: wherein the data acquisition system further comprises a neural network that includes training data sets based on one or more collections of physical objects of a known shape, size, and volume, and wherein determining with the one or more processors at least one of the particle size distribution and the shape distribution of the drill cuttings further comprises training the neural network with the one or more collections of physical objects to generate the training data sets, and querying the neural network with the one or more processors to correlate the known shape, size, and volume of the training data sets to the measurements obtained by the one or more processors. Element 23: further comprising determining a volume rate of the drill cuttings, determining a density of the drill cuttings, and multiplying the volume rate of the drill cuttings with the density of the drill cuttings and thereby obtaining a mass rate of the drill cuttings.

By way of non-limiting example, exemplary combinations applicable to A and B include: Element 1 with Element 2; Element 1 with Element 3; Element 4 with Element 5; Element 4 with Element 6; Element 15 with Element 16; Element 17 with Element 18; and Element 17 with Element 19.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
   receiving an image of drill cuttings with a data acquisition system that includes one or more processors, the drill cuttings originating from a wellbore being drilled and including a plurality of particles;
   analyzing the image of the drill cuttings with the one or more processors by obtaining three two-dimensional distance measurements for each particle and obtaining four angular measurements for each particle; and
   determining with the one or more processors at least one of a particle size distribution of the drill cuttings and a shape distribution of the drill cuttings based on the three two-dimensional distance measurements and the four angular measurements of each particle.

2. The method of claim 1, wherein receiving the image of the drill cuttings with the data acquisition system is preceded by:
   conveying the drill cuttings across a shaker screen of a shaker;
   capturing images of the drill cuttings at or after the shaker screen with one or more imaging devices and thereby generating image data; and
   transmitting the image data to the data acquisition system.

3. The method of claim 2, further comprising illuminating the drill cuttings at or after the shaker screen with a light source that emits a known wavelength of electromagnetic radiation, wherein the light source is selected from the group consisting of a white light source, an incandescent light source, an infrared light source, a laser, one or more light emitting diodes, and any combination thereof.

4. The method of claim 3, wherein the light source includes a plurality of light sources, the method further comprising switching between the plurality of light sources and thereby improving a contrast ratio for at least some of the plurality of particles.

5. The method of claim 1, wherein obtaining the three two-dimensional distance measurements for each particle comprises:
   identifying and measuring a length for each particle;
   identifying and measuring a width for each particle, wherein the measurement for the width bisects the length and is orthogonal thereto; and
   identifying and measuring an intermediate width for each particle, wherein the measurement for the intermediate width is obtained at a mid-way point between an intersection between the length and the width and is orthogonal to the length.

6. The method of claim 5, further comprising comparing measurements for the length, the width, and the intermediate width for a given particle to determine whether the given particle is square, circular, or triangular.

7. The method of claim 5, further comprising averaging measurements for the length, the width, and the intermediate width for each particle to determine a statistical size distribution of the plurality of particles within the drill cuttings.

8. The method of claim 1, wherein a given particle of the plurality of particles is identified as a square-shaped particle when the four angular measurements each range between about 70° and about 110°.

9. The method of claim 1, wherein a given particle of the plurality of particles is identified as a circular-shaped particle when the four angular measurements are each greater than 90°.

10. The method of claim 1, wherein the four angular measurements comprise a first angle, a second angle, a third angle, and a fourth angle, and wherein a given particle of the plurality of particles is identified as a triangle-shaped particle when the fourth angle is zero and a sum of the first, second, and third angles is about 180°.

11. The method of claim 1, further comprising classifying each particle with the one or more processors as one of square, circular, and triangular as based on the three two-dimensional distance measurements and the four angular measurements.

12. The method of claim 1, further comprising:
    capturing images of each particle with at least a first imaging device and a second imaging device, wherein the first imaging device captures images at a first focal plane and the second imaging device captures images at a second focal plane that is different from the first focal plane;
    analyzing the images of each particle from the first and second imaging devices with the one or more processors and obtaining a first depth measurement associated with the first imaging device and a second depth measurement associated with the second imaging device for each particle; and
    determining with the one or more processors a three-dimensional shape of each particle based on the three two-dimensional distance measurements, the four angular measurements, and the first and second depth measurements,
    wherein the three-dimensional shape is selected from the group consisting of a cube, a sphere, and a pyramid.

13. The method of claim 1, wherein the data acquisition system further comprises a neural network that includes training data sets based on one or more collections of physical objects of a known shape, size, and volume, and wherein determining with the one or more processors at least one of the particle size distribution and the shape distribution of the drill cuttings further comprises:
    training the neural network with the one or more collections of physical objects to generate the training data sets; and
    querying the neural network with the one or more processors to correlate the known shape, size, and volume of the training data sets to the measurements obtained by the one or more processors.

14. The method of claim 1, further comprising:
    determining a volume rate of the drill cuttings;
    determining a density of the drill cuttings; and
    multiplying the volume rate of the drill cuttings with the density of the drill cuttings and thereby obtaining a mass rate of the drill cuttings.

15. The method of claim 1, further comprising displaying the at least one of the particle size distribution of the drill cuttings and the shape distribution of the drill cuttings on one or more peripheral devices communicably coupled to the data acquisition system.

16. The method of claim 1, wherein the data acquisition system forms part of an imaging system that includes one or more imaging devices that obtain the image of drill cuttings, the method further comprising:
- sampling a kit of physical objects of a known volume with the one or more imaging devices and thereby obtaining measured volumes with the data acquisition system;
- sampling a kit of physical objects of a known size distribution with the one or more imaging devices and thereby obtaining a measured size distribution with the data acquisition system; and
- determining if the imaging system operates within a predetermined accuracy threshold by comparing at least one of the measured volumes against the known volume and the measured size distribution against the known size distribution.

17. The method of claim 16, further comprising re-calibrating the imaging system when it is determined that the imaging system is operating without the predetermined accuracy threshold.

18. A non-transitory, computer-readable medium programmed with computer executable instructions that, when executed by a processor of a computer unit, perform the method of:
- receiving an image of drill cuttings with a data acquisition system that includes one or more processors, the drill cuttings originating from a wellbore being drilled and including a plurality of particles suspended;
- analyzing the image of the drill cuttings with the one or more processors by obtaining three two-dimensional distance measurements for each particle and obtaining four angular measurements for each particle; and
- determining with the one or more processors at least one of a particle size distribution of the drill cuttings and a shape distribution of the drill cuttings based on the three two-dimensional distance measurements and the four angular measurements of each particle.

19. The non-transitory, computer-readable medium of claim 18, wherein obtaining the three two-dimensional distance measurements for each particle comprises:
- identifying and measuring a length for each particle;
- identifying and measuring a width for each particle, wherein the measurement for the width bisects the length and is orthogonal thereto; and
- identifying and measuring an intermediate width for each particle, wherein the measurement for the intermediate width is obtained at a mid-way point between an intersection between the length and the width and is orthogonal to the length.

20. The non-transitory, computer-readable medium of claim 19, further comprising comparing measurements for the length, the width, and the intermediate width for a given particle to determine whether the given particle is square, circular, or triangular.

21. The non-transitory, computer-readable medium of claim 19, further comprising averaging measurements for the length, the width, and the intermediate width for each particle to determine a statistical size distribution of the plurality of particles within the drill cuttings.

22. The non-transitory, computer-readable medium of claim 18, further comprising classifying each particle with the one or more processors as one of square, circular, and triangular as based on the three two-dimensional distance measurements and the four angular measurements.

23. The non-transitory, computer-readable medium of claim 18, further comprising:
- capturing images of each particle with at least a first imaging device and a second imaging device, wherein the first imaging device captures images at a first focal plane and the second imaging device captures images at a second focal plane that is different from the first focal plane;
- analyzing the images of each particle from the first and second imaging devices with the one or more processors and obtaining a first depth measurement associated with the first imaging device and a second depth measurement associated with the second imaging device for each particle; and
- determining with the one or more processors a three-dimensional shape of each particle based on the three two-dimensional distance measurements, the four angular measurements, and the first and second depth measurements,
- wherein the three-dimensional shape is selected from the group consisting of a cube, a sphere, and a pyramid.

24. The non-transitory, computer-readable medium of claim 18, wherein the data acquisition system further comprises a neural network that includes training data sets based on one or more collections of physical objects of a known shape, size, and volume, and wherein determining with the one or more processors at least one of the particle size distribution and the shape distribution of the drill cuttings further comprises:
- training the neural network with the one or more collections of physical objects to generate the training data sets; and
- querying the neural network with the one or more processors to correlate the known shape, size, and volume of the training data sets to the measurements obtained by the one or more processors.

25. The non-transitory, computer-readable medium of claim 18, further comprising:
- determining a volume rate of the drill cuttings;
- determining a density of the drill cuttings; and
- multiplying the volume rate of the drill cuttings with the density of the drill cuttings and thereby obtaining a mass rate of the drill cuttings.

* * * * *